United States Patent
Martin (10) Patent No.: US 10,231,682 B2
(45) Date of Patent: Mar. 19, 2019

(54) APPARATUSES FOR MANIPULATING A SENSOR

(71) Applicant: Radiographic Paddle, LLC, San Antonio, TX (US)

(72) Inventor: Brent Douglas Martin, San Antonio, TX (US)

(73) Assignee: Radiographic Paddle, LLC, San Antonio, TX (US)

( * ) Notice: Subject to any disclaimer, the term of this patent is extended or adjusted under 35 U.S.C. 154(b) by 0 days.

(21) Appl. No.: 15/880,516

(22) Filed: Jan. 25, 2018

(65) Prior Publication Data

US 2018/0214099 A1  Aug. 2, 2018

Related U.S. Application Data

(60) Provisional application No. 62/451,711, filed on Jan. 28, 2017.

(51) Int. Cl.
| | | |
|---|---|---|
| *A61B 6/00* | (2006.01) | |
| *H05K 9/00* | (2006.01) | |
| *G01T 1/175* | (2006.01) | |
| *A61B 6/10* | (2006.01) | |
| *H01F 7/02* | (2006.01) | |
| *G01T 7/00* | (2006.01) | |
| *A61B 6/14* | (2006.01) | |

(52) U.S. Cl.
CPC ............ *A61B 6/4405* (2013.01); *A61B 6/107* (2013.01); *A61B 6/145* (2013.01); *G01T 1/175* (2013.01); *G01T 7/00* (2013.01); *H01F 7/0252* (2013.01); *H05K 9/0081* (2013.01)

(58) Field of Classification Search
CPC ............ A61B 1/00016; A61B 1/00009; A61B 1/00032; A61B 1/00039; A61B 1/00055; A61B 1/00101; A61B 1/041; A61B 1/053; A61B 1/0684; A61B 5/00; G02B 23/2461; G02B 23/2484; G06F 1/1601; G06F 1/1605; G06F 3/011
USPC ................ 600/109, 160, 300, 309; 345/156; 250/491.1, 526
See application file for complete search history.

(56) References Cited

U.S. PATENT DOCUMENTS

| | | | |
|---|---|---|---|
| 5,631,943 A | 5/1997 | Miles | |
| 6,038,287 A | 3/2000 | Miles | |
| 7,626,569 B2 * | 12/2009 | Lanier | .............. G06F 1/1601 345/156 |
| 8,801,433 B1 | 8/2014 | Charlton | |
| 8,928,746 B1 * | 1/2015 | Stevrin | .............. G02B 23/2461 348/68 |
| 9,247,867 B2 * | 2/2016 | Baum | ................ A61B 1/00013 |
| 9,710,414 B2 | 7/2017 | Liang | |
| 2003/0186193 A1 | 10/2003 | Comfort | |
| 2003/0207229 A1 | 11/2003 | Wong | |

(Continued)

*Primary Examiner* — David A Vanore
(74) *Attorney, Agent, or Firm* — David A. Topmiller, Esq.

(57) ABSTRACT

Apparatuses are disclosed for permitting a user to manipulate a sensor. The apparatuses have a handle, an arm, and a sensor mounting head. The sensor may be removably affixed to the sensor mounting head by the user. The arm is permanently flexible so that the user may adjust the position of the affixed sensor to any arbitrary position with respect to the handle. The apparatuses are capable of using wired and wireless sensors. In one embodiment, the handle contains a power source which supplies energy to operate a wireless sensor.

21 Claims, 6 Drawing Sheets

(56) References Cited

U.S. PATENT DOCUMENTS

| | | |
|---|---|---|
| 2005/0220272 A1 | 10/2005 | Glazer |
| 2006/0020176 A1* | 1/2006 | Berall .................... A61B 1/267 600/300 |
| 2010/0190129 A1 | 7/2010 | Paz |
| 2011/0046637 A1 | 2/2011 | Patel et al. |
| 2011/0208007 A1 | 8/2011 | Shohat et al. |
| 2013/0172696 A1* | 7/2013 | Riesinger ................. A61B 5/01 600/309 |
| 2014/0343360 A1 | 11/2014 | Shohat et al. |
| 2016/0000300 A1* | 1/2016 | Williams ........... A61B 1/00016 600/109 |
| 2016/0207190 A1 | 7/2016 | Balz et al. |
| 2017/0043474 A1 | 2/2017 | Balz et al. |
| 2017/0095229 A1 | 4/2017 | Mander et al. |
| 2017/0127930 A1 | 5/2017 | Shohat et al. |
| 2018/0214099 A1* | 8/2018 | Martin ................. A61B 6/4405 |

* cited by examiner

APPARATUSES FOR MANIPULATING A SENSOR

CROSS REFERENCE TO RELATED APPLICATION

This application claims the benefit of provisional application Ser. No. 62/451,711, filed Jan. 28, 2017, the disclosure of which is incorporated herein by reference.

TECHNICAL FIELD

The present disclosure generally relates to apparatuses that assist a user in manipulating a sensor, such as an X-ray sensor. The apparatus may facilitate the positioning of the sensor inside small cavities by allowing the user to adjust the relative position of the sensor with respect to the handle. In this fashion, the user may manipulate and position the sensor inside the cavity in a manner that may allow the sensor to operate more effectively.

BACKGROUND

As background, there are numerous apparatuses available today which allow a user to manipulate a tool or sensor. These apparatuses have a handle to allow the user to grasp it, and they typically have a sensor mounting head for installing and retaining various tools or sensors. In some of these apparatuses, the user may adjust the position of the tool or sensor with respect to the handle in order to facilitate the use of the tool or the sensor by the user. However, none have a permanently flexible arm which permits the user to adjust the tool or sensor to any arbitrary position with respect to the handle. In addition, none have a universal sensor mounting head to which tools and/or sensors of various types from multiple suppliers may be easily affixed and removed. Furthermore, none have the capability of providing a biological cover over the handle and the capability of accepting a radiation shield on the handle to protect the user from X-rays and/or other potentially harmful radiation. The apparatuses described herein overcome all of these limitations.

As an example of the prior art, U.S. Pat. No. 8,801,433 discloses a dental instrument which is capable of accepting a plurality of different tools, any one of which may be installed at the end of the instrument. When installed, the tool may be adjusted to a desired rotational angular position, relative to the handle axis. After its position is adjusted, the tool may be secured by tightening a threaded locking pin located in the handle, which holds the tool in place during use. However, this instrument only permits the tool to be adjusted in one angular axis with respect to the handle. It does not have a permanently flexible arm to allow the tool to be adjusted to any arbitrary position relative to the handle.

As another example of the prior art, U.S. Pat. No. 9,710,414 teaches an interchangeable wireless sensing apparatus for mobile or networked devices. The apparatus comprises a common base unit (CBU) and an interchangeable sensing apparatus (ISA). The ISA may comprise different types of sensors, such as image sensors and multichannel ECG/EEG sensors. The CBU may contain a power source (e.g., a battery), which may provide the power needed to operate both the CBU and the ISA. In addition, the CBU has a mounting head for the ISA which provides both a mechanical and an electrical connection. However, the ISA is restricted to adjustments in two angular axes with respect to the handle; the ISA cannot be adjusted to any arbitrary position relative to the CBU.

Yet another example of the prior art is U.S. Patent Application Publication 2005/0220272, which discloses a wireless digital X-ray sensor with a positioning apparatus. The sensor includes a CCD or CMOS image sensor which is attached to the distal end of a bite block portion through a hinge assembly. When placed in the patient's mouth, the bite block portion allows for further positioning of the sensor within the mouth by allowing a variety of operative positions relative to the bite block portion. However, the sensor is restricted to adjustments in two orthogonal angular axes with respect to the bite block and cannot be adjusted to any arbitrary position relative to the bite block.

As another example of the prior art, U.S. Patent Application Publication 2013/0172696 teaches a hand-held measuring device with an exchangeable probe. The device includes a handle, called an instrument housing, and it is capable of accepting different types of sensors, called probes. The instrument housing may contain a battery which is used to power the device (including the sensor). The types of sensors which may be installed on the device include pH sensors and/or temperature sensors. In addition, the handle may include a display which is capable of displaying information from the sensor. However, like the previous prior art examples, this device does not allow the sensor to be arbitrarily adjusted to any position with respect to the handle. The aforementioned examples of prior art and their corresponding limitations are intended to be illustrative and not exhaustive.

The apparatuses disclosed herein overcome the inherent disadvantages in each of the prior art apparatuses by providing a universal sensor mounting head and permitting the user to adjust the sensor to any arbitrary position with respect to the handle. Moreover, the apparatuses are capable of providing a biological cover over the handle which may protect the user from potentially dangerous bacteria or viruses. Additionally, since the apparatuses are held by the user, patients may be able to hold the apparatus in place themselves. On deceased patients, sedated patients, and veterinary patients, the user holds the apparatus in place. Some of the prior art devices are designed for dental patients to hold them by biting on them, and the user must place their hands directly in the X-ray field. With the apparatuses disclosed herein, the physical distance as well as the radiation shield may protect the user from the radiation of the X-ray field.

Limitations in the prior art will become apparent to those skilled in the art after reviewing the specification below and the corresponding drawings.

SUMMARY

In one embodiment, an apparatus for manipulating a sensor is disclosed, the apparatus comprising a handle, an arm, and a sensor mounting head, wherein: the arm is permanently flexible and comprises a first end and a second end; the handle is mechanically coupled to the arm at the first end, and the sensor mounting head is mechanically coupled to the arm at the second end; the sensor is capable of being removably affixed to the sensor mounting head; and the sensor comprises a sensor axis such that the sensor is capable of being affixed to the sensor mounting head within a range of 0 to 360 degrees about the sensor axis with respect to the sensor mounting head.

In another embodiment, an apparatus for manipulating a sensor is disclosed, the apparatus comprising a handle, an arm, and a sensor mounting head, wherein: the arm is permanently flexible and comprises a first end and a second end; the handle is mechanically coupled to the arm at the first end, and the sensor mounting head is mechanically coupled to the arm at the second end; the sensor is capable of being removably affixed to the sensor mounting head; the sensor comprises a sensor axis such that the sensor is capable of being affixed to the sensor mounting head within a range of 0 to 360 degrees about the sensor axis with respect to the sensor mounting head; the handle comprises a power source capable of supplying energy to the sensor; and the sensor mounting head further comprises a first interface, wherein the first interface is electrically coupled to the power source and is capable of supplying energy to the sensor when the sensor is affixed to the sensor mounting head.

BRIEF DESCRIPTION OF THE DRAWINGS

The embodiments set forth in the drawings are illustrative and exemplary in nature and not intended to limit the inventions defined by the claims. The following detailed description of the illustrative embodiments can be understood when read in conjunction with the following drawings, where like structure is indicated with like reference characters and in which:

DETAILED DESCRIPTION

The embodiments described herein generally relate to apparatuses for manipulating a sensor. The apparatus may comprise a handle, an arm, and a sensor mounting head to which a sensor may be removably affixed. The sensor may be an X-ray sensor or any other type of sensor. The apparatus may further comprise a radiation shield which may reduce the amount of radiation exposure to a user of the apparatus.

Figure 1:
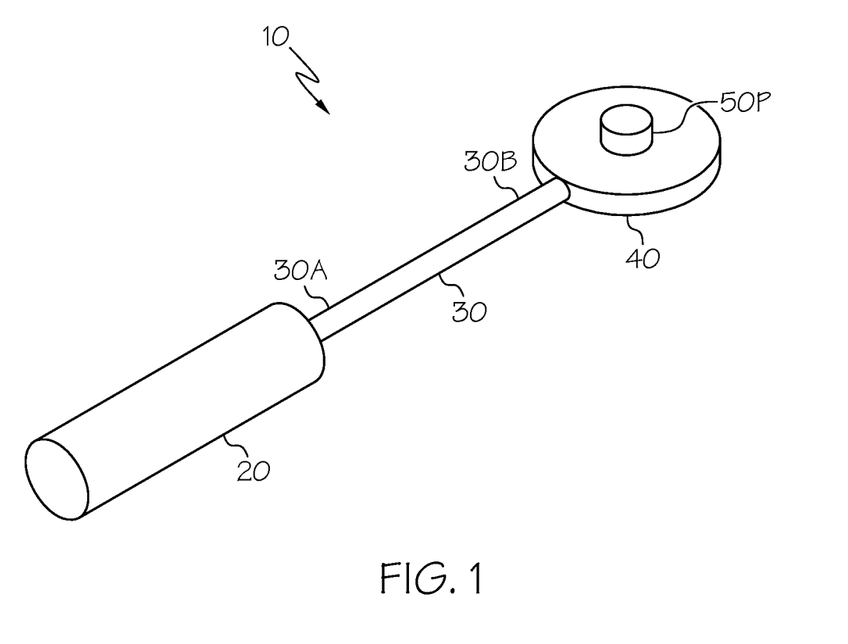
FIG. 1 depicts an apparatus for manipulating a sensor according to one or more embodiments shown and described herein.

FIG. 1 depicts an apparatus 10 for manipulating a sensor (not shown). The apparatus includes a handle 20, an arm 30, and a sensor mounting head 40. The handle 20 may be substantially linear and may be designed to fit comfortably into the hand of the user. The handle 20 may be comprised of metal, plastic, or any suitable material. In addition, the handle 20 may be substantially rigid in order to facilitate gripping and manipulating by the user. The arm 30 may be permanently flexible and may comprise a first end 30A and a second end 30B. The arm 30 may be mechanically coupled to the handle 20 at the first end 30A, and the arm 30 may be mechanically coupled to the sensor mounting head 40 at the second end 30B. The arm 30 may be comprised of metal, plastic, or any suitable material or combinations of materials. For example, in one embodiment, the arm 30 may comprise aluminum or an aluminum alloy. As another example, the arm 30 may comprise aluminum surrounded by a plastic jacket. The arm 30 may allow the user to arbitrarily position the sensor mounting head 40 with respect to the handle 20. A sensor (not shown) may be removably affixed to the sensor mounting head 40 by the user. It is contemplated that different types of sensors may be affixed to the sensor mounting head 40.

As used herein, the phrase "permanently flexible" means to be flexible so as to allow a user of the apparatus 10 to bend the arm 30 into any suitable shape such that the sensor mounting head 40 (and the corresponding sensor affixed thereto) may be arbitrarily positioned with respect to the handle 20. This may allow the user to position the sensor mounting head 40 in a manner that may increase the effectiveness of the sensor. Once the user has bent the arm 30 so that the sensor mounting head 40 and sensor are in the desired position with respect to the handle 20, the arm 30 may permanently remain in that particular shape until the user decides to re-position the sensor mounting head 40 again. Thus, the arm 30 may be capable of being bent with sufficient force from the user, but it is also capable of retaining its shape when the sensor is manipulated by the user.

Figure 2A:
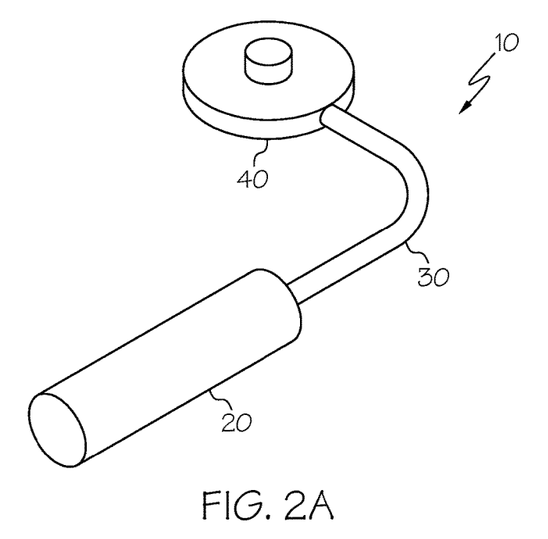
FIGS. 2A and 2B illustrate apparatuses for manipulating a sensor according to one or more embodiments shown and described herein.
Figure 2B:
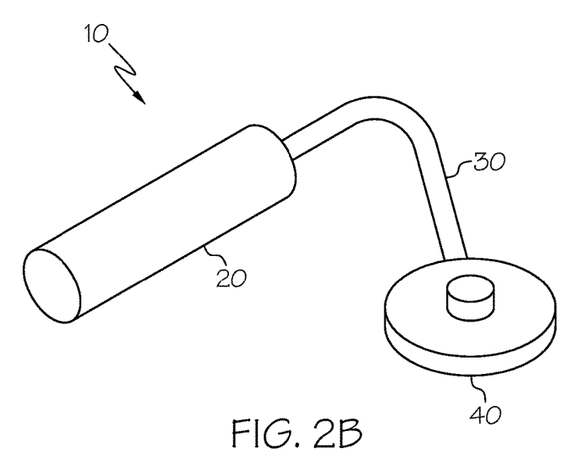

FIGS. 2A and 2B show an apparatus 10 for manipulating a sensor (not shown) in a condition in which the arm 30 had been bent in order to position the sensor mounting head 40 at an arbitrary position with respect to the handle 20. In FIG. 2A, the sensor mounting head 40 has been positioned to the left of the handle 20. In FIG. 2B, the sensor mounting head 40 has been positioned to the right of the handle 20. Although these are relatively simple examples of how the sensor mounting head 40 may be arbitrarily positioned with respect to the handle 20, it is contemplated that more complex positioning is possible. Once the sensor mounting head 40 has been placed in a position desired by the user, the arm 30 may retain its shape and, thus, keep the sensor mounting head 40 at the same relative position with respect to the handle 20 until the user applies more force. It is also contemplated that the sensor mounting head 40 may be rotated with respect to the arm 30. In this manner, the sensor mounting head 40 may be truly positioned in an arbitrary manner with respect to the handle 20.

Figures 3, 4:
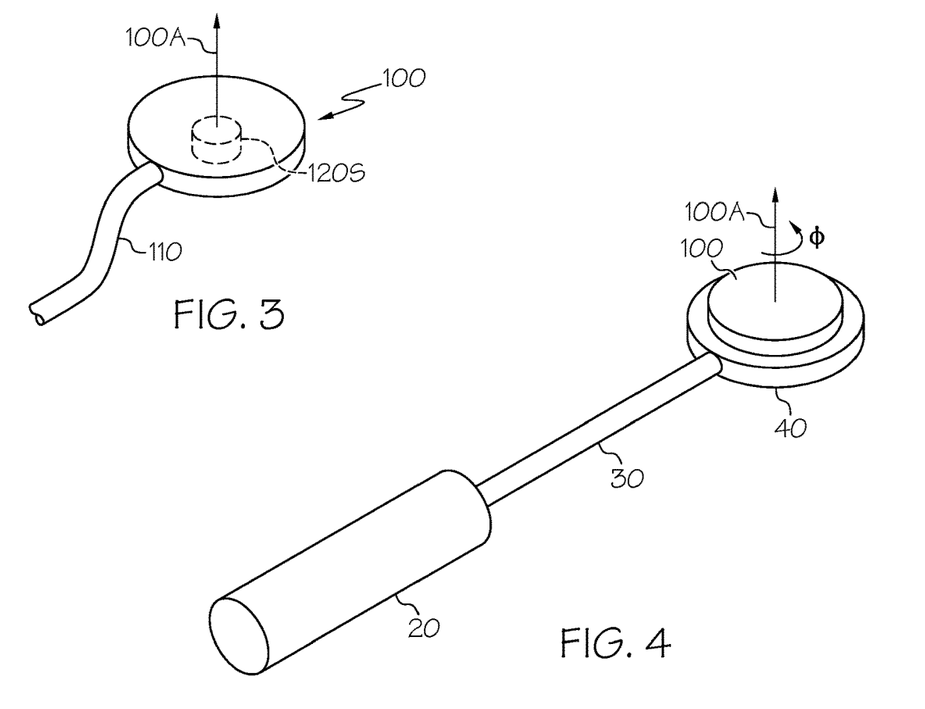
FIG. 3 shows a sensor according to one or more embodiments shown and described herein.
FIG. 4 depicts an apparatus for manipulating a sensor according to one or more embodiments shown and described herein.

Referring to FIG. 3, a sensor 100 is shown which may be removably affixed to the sensor mounting head (not shown). The sensor 100 may be an X-ray sensor or other type of sensor. The sensor 100 may have a cable 110 which may be connected to other equipment (not shown) capable of reading and/or interpreting the data captured by the sensor 100. For wireless sensors, the cable 110 may be omitted, and the sensor data may be transmitted wirelessly. The cable 110 may be positioned near the handle for the convenience of the user. In one embodiment, the handle may have a slot into which the cable 110 may be inserted in order to reduce the likelihood of the cable 110 interfering with operation of the apparatus. The sensor 100 may also have an alignment slot 120S which may facilitate the installation of the sensor 100 into the sensor mounting head of the apparatus. In addition, the sensor 100 may comprise a sensor axis 100A which may be substantially perpendicular to the surface of the sensor 100. The sensor 100 may be affixed to the sensor mounting head within a range of 0 to 360 degrees (i.e., any angle) about the sensor axis 100A with respect to the sensor mounting head.

FIG. 4 depicts an apparatus for manipulating a sensor 100 wherein the sensor 100 is affixed to the sensor mounting head 40 of the apparatus. The sensor 100 may be affixed to the sensor mounting head 40 within a range of 0 to 360 degrees (i.e., any rotational angle φ) about the sensor axis 100A. The user may adjust the relative position of the sensor 100 with respect to the handle 20 by bending the permanently flexible arm 30 in the desired manner. The user may then manipulate the sensor 100 by grasping the handle 20 of the apparatus and positioning the sensor 100 as desired. In this figure, the cable from the sensor 100 is not shown.

When the sensor 100 is being affixed to the sensor mounting head 40, the sensor may be disposed at an angle φ of 0 to 360 degrees about the sensor axis 100A. However, once the sensor 100 is affixed to the sensor mounting head 40, the sensor 100 may be prevented from rotating about the sensor axis 100A by any number of techniques. For example, the surface of the sensor 100 and/or the surface of the sensor mounting head 40 which are in contact with one another may have a texture or quality which may prevent rotation. Other techniques may be employed, as is known in the art.

Figure 5:
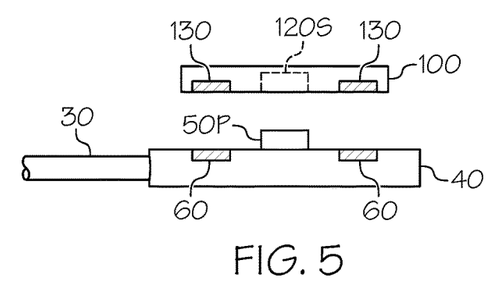
FIG. 5 shows a sensor and a sensor mounting head according to one or more embodiments shown and described herein.

FIG. 5 shows one embodiment of how the sensor 100 may be affixed to the sensor mounting head 40. It may be beneficial to provide an alignment mechanism to facilitate the affixing of the sensor 100 to the sensor mounting head 40. This alignment mechanism may prevent the sensor 100, when affixed to the sensor mounting head 40, from moving relative to the sensor mounting head 40 during use. In one embodiment, the sensor 100 may comprise an alignment slot 120S, and the sensor mounting head 40 may comprise an alignment pin 50P. The alignment slot 120S and the alignment pin 50P may be mechanically complimentary, such that, when the sensor 100 is affixed to the sensor mounting head 40, the alignment pin 50P of the sensor mounting head 40 may serve as a guide and may be inserted into the alignment slot 120S of the sensor 100. As discussed previously, the sensor 100 may be installed at any suitable angle about the sensor axis with respect to the sensor mounting head 40. Other types of alignment mechanisms may be used, as is known in the art.

The sensor mounting head 40 may further comprise one or more first retaining elements 60, and the sensor 100 may further comprise one or more second retaining elements 130. When the sensor 100 is affixed to the sensor mounting head 40, an attractive force between the first retaining elements 60 and the second retaining elements 130 may cause the sensor 100 to remain affixed until removed by the user. The first retaining elements 60 may comprise one or more magnets, and the second retaining elements 130 may comprise one or more ferromagnetic elements. In another embodiment, the first retaining elements 60 may comprise one or more ferromagnetic elements, and the second retaining elements 130 may comprise one or more magnets. In yet another embodiment, both the first retaining elements 60 and the second retaining elements 130 may comprise magnets. The one or more magnets may comprise Samarium-Cobalt magnets, neodymium magnets, or any suitable type of magnets. The ferromagnetic elements may comprise steel, ferrous alloys, nickel, or any other type of material that may be attracted by a magnet field. Although the retaining elements are shown in FIG. 5 as being physically separate from the alignment slot 120S and the alignment pin 50P, it is contemplated that the one or more second retaining elements may be disposed proximate to the alignment slot 120S and/or the one or more first retaining element may be disposed within the alignment pin 50P. For example, one or more ferromagnetic elements may be proximate to the alignment slot 120S, and the alignment pin 50P may comprise one or more magnets.

The use of the first and second retaining elements as described above and other similar techniques may allow the sensor 100 to be easily affixed to and easily removed from the sensor mounting head 40 by the user. As such, the apparatus may be considered to have a "quick connect/disconnect" feature regarding the sensor 100. That is, the user may very quickly affix the sensor 100 to the sensor mounting head 40 by simply disposing the sensor 100 proximate to the sensor mounting head 40 such that the attractive force of the retaining elements pulls the sensor 100 toward the sensor mounting head 40, thus affixing the sensor 100 thereto. This may also allow the user to change sensors very quickly by removing the first sensor by simply pulling it away from the sensor mounting head 40 and affixing the second sensor by disposing it proximate to the sensor mounting head 40 as described above.

Other techniques may also be used to affix the sensor 100 to the sensor mounting head 40, as is known in the art. For example, the alignment slot 120S may comprise a snap ring which may be mechanically coupled to a corresponding groove in the alignment pin 50P such that, when affixed, the snap ring is disposed within the groove. In this fashion, the snap ring and groove may affix the sensor 100 to the sensor mounting head 40 until the sensor 100 is removed by the user. It is anticipated that other techniques of affixing the sensor 100 to the sensor mounting head 40 may be used as well.

As discussed above, the sensor 100 may be prevented from rotating about the sensor axis when affixed to the sensor mounting head 40. In one embodiment, this may be done by configuring the surface of the sensor 100 and/or the surface of the sensor mounting head 40 which are in contact with one another to have a texture or quality which may prevent rotation. In another embodiment, rotation may be prevented by adding splines to the alignment slot 120S and/or the alignment pin 50P. In yet another embodiment, the sides of the alignment slot 120S and alignment pin 50P may be tapered in a complementary manner such that, when the sensor 100 is affixed to the sensor mounting head 40, the tapered sides are in contact and prevent rotation. Other techniques may be used to prevent the sensor 100 from rotating when affixed to the sensor mounting head 40, as is known in the art.

Figure 6:
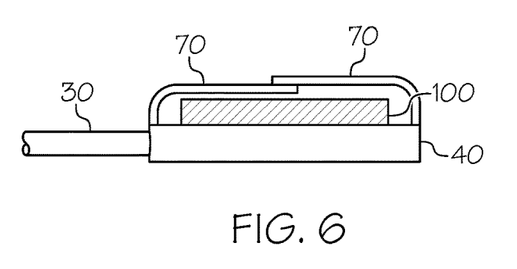
FIG. 6 illustrates a sensor and a sensor mounting head according to one or more embodiments shown and described herein.

FIG. 6 illustrates an apparatus comprising a sensor mounting head 40 having one or more retaining straps 70 which are capable of affixing the sensor 100 to the sensor mounting head 40. The one or more retaining straps 70 may be flexible in order to allow the sensor 100 to be installed and removed easily by the user. The one or more retaining straps 70 may be configured to attach to one another so as to affix the sensor 100 to the sensor mounting head 40. For example, the one or more retaining straps 70 may be Velcro® or any other suitable material. The one or more retaining straps 70 may be easily moved out of the way to allow the use to remove the sensor 100 when desired.

Figure 7:
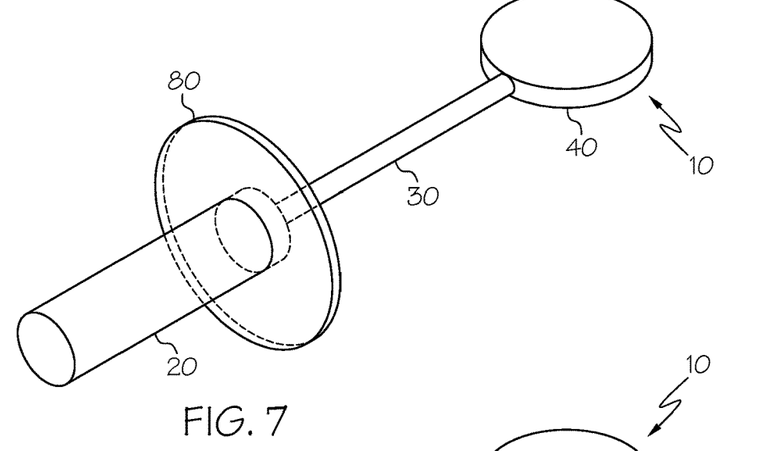
FIG. 7 depicts an apparatus having handle with a radiation shield according to one or more embodiments shown and described herein.

FIG. 7 depicts an apparatus 10 having a handle 20 comprising a radiation shield 80. The radiation shield 80 may be capable of reducing electromagnetic radiation directed toward the handle 20 and, consequently, to a user whose hand is grasping the handle 20. The radiation shield 80 may be permanently affixed to the handle 20, or it may be removably affixed to the handle 20. The radiation shield 80 may be configured to be proximate to where the handle 20 is mechanically coupled to the arm 30. The radiation shield 80 may reduce the electromagnetic radiation to the handle 20 when, for example, the type of sensor affixed to the sensor mounting head 40 is an X-ray sensor capable of sensing radiation from an X-ray source. This may occur when the user is grasping the handle 20 while taking X-ray images of a patient. The X-rays being sensed by the X-ray sensor may scatter due to a number of factors, and the radiation shield 80 may reduce the intensity of this stray radiation directed toward the handle 20. The radiation shield 80 may be substantially in the shape of a disk, and it may be comprised of lead or any other suitable material. In general, the physical distance between the sensor and the user's hand as well as the radiation shield 80 combine to reduce or substantially eliminate the radiation to the user of the apparatus 10.

Figure 8:
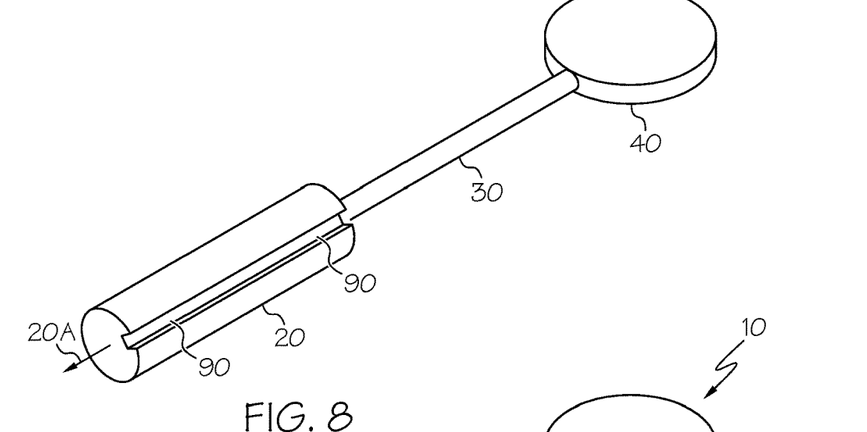
FIG. 8 shows an apparatus having handle with a cable slot according to one or more embodiments shown and described herein.

FIG. 8 shows an apparatus 10 comprising a handle 20 having a cable slot 90. The cable slot 90 may be substantially parallel to an axis 20A of the handle 20. When the affixed sensor comprises a cable mechanically coupled to the sensor, the cable may be inserted into the cable slot 90, which may allow the cable from the sensor to be positioned so that is it out of the way of the user. As such, it may facilitate the usage of the apparatus 10 since the cable, when inserted into the cable slot 90, may reduce any potential interference of the cable with the positioning and operation of the apparatus 10. The cable slot 90 may have a mechanism which may facilitate in retaining the cable inside the cable slot 90. For example, the mechanism may include a flap or a cover.

Figure 9:
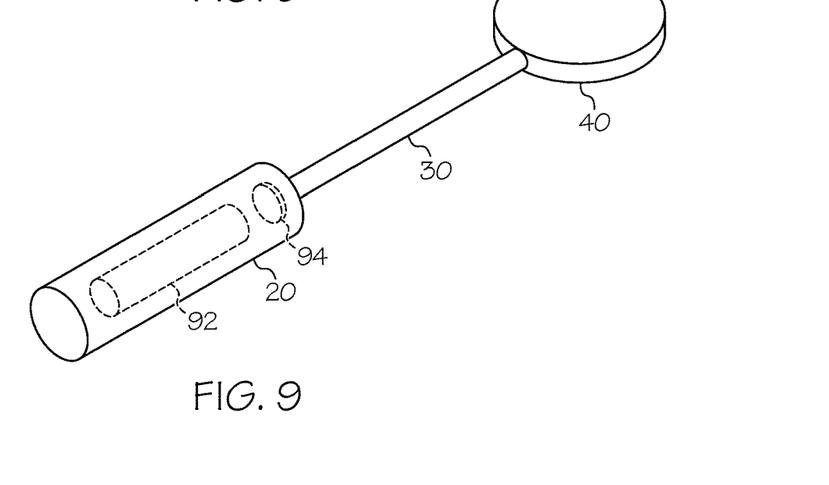
FIG. 9 illustrates an apparatus having handle with a power source and wireless data transmitter according to one or more embodiments shown and described herein.

FIG. 9 illustrates an apparatus 10 wherein the handle 20 comprises a power source 92. The power source may be capable of supply energy to operate the sensor, and the power source 92 may be electrically coupled to the sensor when the sensor is affixed to the sensor mounting head 40. The power source 92 may comprise a battery or any other suitable device. When the power source 92 is a battery, the battery may be either rechargeable or non-rechargeable. The power source 92 may be coupled to the sensor through wires inside the arm 30. The wires may be coupled to the sensor via a standard connector or via a wireless means. For example, the wires may be coupled to the sensor via near-field communication (NFC) such that the power source 92 is capable of supplying power to the sensor via the NFC.

The handle 20 may further comprise a wireless data transmitter 94 which may be electrically coupled to the sensor. The wireless data transmitter 94 may be capable of receiving data from the sensor and wirelessly transmitting the data to a receiving device, such as a computer or tablet. The wireless data transmitter 94 may permit different types of sensors to be affixed to the sensor mounting head 40 and may provide a common electrical interface thereto. For example, a sensor affixed to the sensor mounting head 40 may transmit sensor data to the wireless data transmitter 94 through an interface cable (e.g., one or more wires) that is disposed in the arm 30. The wireless data transmitter 94 may, in turn, wirelessly transmit the sensor data to a receiving device.

Figure 10:
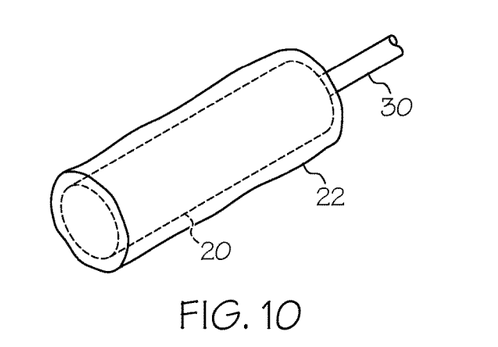
FIG. 10 depicts a biological barrier according to one or more embodiments shown and described herein.

FIG. 10 depicts a biological barrier 22 surrounding the handle 20. The biological barrier 22 may be removable and may reduce the probability of biological material present on the handle 20 from coming into contact with a hand of a user grasping the handle 20 through the biological barrier 22. The biological barrier 22 may be rigid or flexible and may comprise, for example, plastic or film. The biological barrier 22 may also be referred to as personal protective equipment (PPE). The biological material may include bacteria, viruses, funguses, and so forth.

Figure 11A:
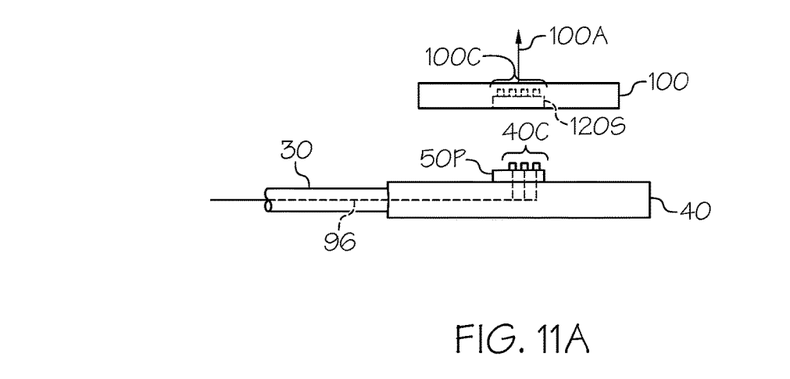
FIGS. 11A and 11B show electrical interfaces between the sensor mounting head and the sensor according to one or more embodiments shown and described herein.
Figure 11B:
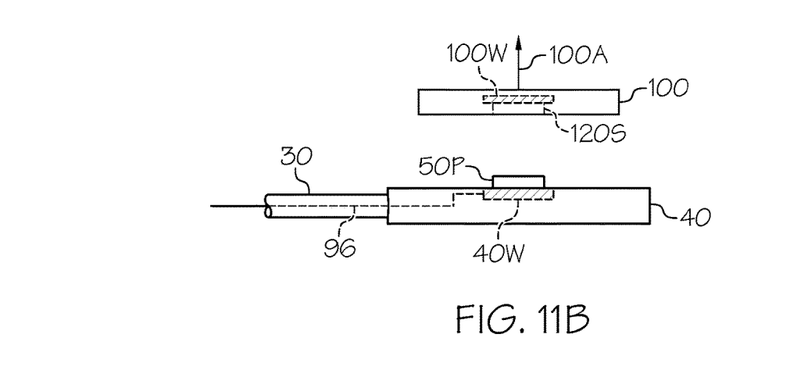

FIGS. 11A and 11B illustrate possible techniques for electrical connectivity between the sensor 100 and the sensor mounting head 40. In FIG. 11A, the sensor mounting head 40 may comprise a first connector 40C, which may be part of the first interface. The first connector 40C may be coupled to the power source and/or wireless data transmitter via an interface cable 96, which may comprise one or more individual wires. The first connector 40C may be configured such that it is electrically coupled to a second connector 100C on the sensor 100 when the sensor 100 is affixed to the sensor mounting head 40. In this case, the power source may provide power to operate the sensor 100 through the electrical coupling of the first connector 40C and second connector 100C. In addition, data from the sensor 100 may be transmitted through the first connector 40C and second connector 100C to the wireless data transmitter.

If the sensor mounting head 40 has an alignment pin 50P, the first connector 40C may be disposed on the alignment pin 50P. Likewise, if the sensor 100 has an alignment slot 120S, the second connector 100C may be disposed in the alignment slot 120S. In addition, the first connector 40C may comprise one or more electrical pins, and the second connector 100C may comprise one or more electrical pins which are complementary to the electrical pins in the first connector 40C. This may allow these complementary pins to make contact with one another when the sensor 100 is affixed to the sensor mounting head 40, and the alignment pin 50P is disposed in the alignment slot 120S. The electrical pins may be designed so they make electrical contact with one another when the sensor 100 is rotated from 0 to 360 degrees about the sensor axis 100A. For example, electrical pins of the second electrical connector 100C may be annular in shape so that the electrical pins of the first electrical connector 40C may be able to make contact independent of the angle that the sensor 100 is affixed with respect to the sensor mounting head 40.

In FIG. 11B, the sensor mounting head 40 may comprise a first wireless interface 40W, which may be part of the first interface. The first wireless interface 40W may be coupled to the power source and/or wireless data transmitter via an interface cable 96, which may comprise one or more wires. The first wireless interface 40W may be wirelessly coupled to a second wireless interface 100W on the sensor 100 when the sensor 100 is affixed to the sensor mounting head 40. In this case, the power source may provide power to operate the sensor 100 through the wireless coupling of the first wireless interface 40W and second wireless interface 100W. In addition, data from the sensor 100 may be transmitted through the first wireless interface 40W and second wireless interface 100W to the wireless data transmitter.

In one embodiment, the first wireless interface 40W and the second wireless interface 100W may communicate via near field communication (NFC). That is, power and/or data may be transmitted via an electromagnetic field. In this embodiment, the first wireless interface 40W and the second wireless interface 100W may each comprise an electrical coil electrically coupled to each other when the sensor 100 is affixed to the sensor mounting head 40. Such a wireless interface may facilitate the cleaning and/or sterilization of the sensor 100 and the sensor mounting head 40 (as well as the entire apparatus) since a wireless interface may permit a smoother surface than an interface having a connector.

Figure 12A:
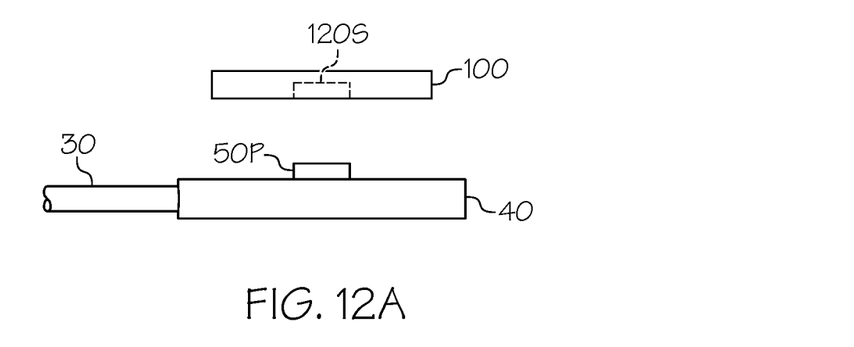
FIGS. 12A and 12B illustrate sensors and sensor mounting heads according to one or more embodiments shown and described herein.
Figure 12B:
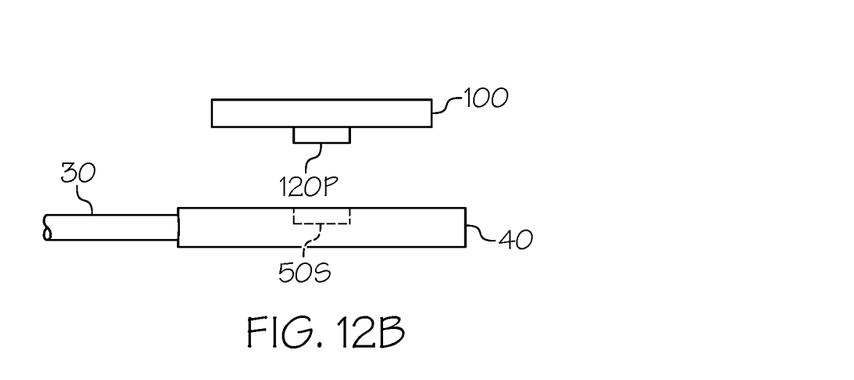

FIG. 12A shows a sensor 100 and a sensor mounting head 40 according to one embodiment. The sensor 100 may comprise an alignment slot 120S, and the sensor mounting head 40 may comprise an alignment pin 50P. As discussed above, the alignment slot 120S and the alignment pin 50P may be mechanically complimentary so that, when the sensor 100 is affixed to the sensor mounting head 40, the alignment pin 50P may be inserted into the alignment slot 120S. This may assist the user in guiding and positioning the sensor 100 onto the sensor mounting head 40 during the affixing process. Also, this may prevent the sensor 100 from moving laterally with respect to the sensor mounting head 40. FIG. 12B depicts another embodiment of the alignment pin 120P and the alignment slot 50S which is essentially inverted from the embodiment shown in FIG. 12A. In FIG. 12B, the sensor 100 comprises an alignment pin 120P, and the sensor mounting head 40 comprises an alignment slot 50S. Other methods of guiding and positioning the sensor 100 onto the sensor mounting head 40 are contemplated as well.

While particular embodiments and aspects of the present invention have been illustrated and described herein, various other changes and modifications may be made without departing from the spirit and scope of the invention. Moreover, although various inventive aspects have been described herein, such aspects need not be utilized in combination. It is therefore intended that the appended claims cover all such changes and modifications that are within the scope of this invention.

What is claimed is:

1. An apparatus for manipulating a sensor, the apparatus comprising a handle, an arm, and a sensor mounting head, wherein:
    the arm is permanently flexible and comprises a first end and a second end;
    the handle is mechanically coupled to the arm at the first end, and the sensor mounting head is mechanically coupled to the arm at the second end;
    the sensor is capable of being removably affixed to the sensor mounting head;
    the sensor comprises a sensor axis such that the sensor is capable of being affixed to the sensor mounting head within a range of 0 to 360 degrees about the sensor axis with respect to the sensor mounting head; and
    the sensor mounting head comprises one or more first retaining elements, and the sensor comprises one or more second retaining elements such that an attractive force between the one or more first retaining elements and the one or more second retaining elements affixes the sensor to the sensor mounting head.

2. The apparatus of claim 1, wherein
    the one or more first retaining elements are magnets and the one or more second retaining elements are ferromagnetic elements, or the one or more first retaining elements are magnets and the one or more second retaining elements are magnets, or the one or more first retaining elements are ferromagnetic elements and the one or more second retaining elements are magnets.

3. The apparatus of claim 2 further comprising a radiation shield mechanically coupled to the handle.

4. The apparatus of claim 3, wherein the radiation shield comprises substantially lead.

5. The apparatus of claim 1, wherein the sensor mounting head comprises one or more retaining straps capable of affixing the sensor to the sensor mounting head.

6. The apparatus of claim 1 further comprising a radiation shield mechanically coupled to the handle.

7. The apparatus of claim 6, wherein the radiation shield comprises substantially lead.

8. The apparatus of claim 1, wherein the apparatus further comprises a removable biological barrier substantially surrounding the handle, such that the biological barrier reduces the probability of biological material present on the handle from coming into contact with a hand of a user grasping the handle through the biological barrier.

9. The apparatus of claim 1, wherein the handle comprises a cable slot substantially parallel to an axis of the handle, the sensor further comprises a cable mechanically coupled to the sensor, and, when the sensor is affixed to the sensor mounting head, the cable is capable of being inserted into the cable slot.

10. An apparatus for manipulating a sensor, the apparatus comprising a handle, an arm, and a sensor mounting head, wherein:
    the arm is permanently flexible and comprises a first end and a second end;
    the handle is mechanically coupled to the arm at the first end, and the sensor mounting head is mechanically coupled to the arm at the second end;
    the sensor is capable of being removably affixed to the sensor mounting head;
    the sensor comprises a sensor axis such that the sensor is capable of being affixed to the sensor mounting head within a range of 0 to 360 degrees about the sensor axis with respect to the sensor mounting head;
    the sensor mounting head comprises one or more first retaining elements, and the sensor comprises one or more second retaining elements such that an attractive force between the one or more first retaining elements and the one or more second retaining elements affixes the sensor to the sensor mounting head;
    the handle comprises a power source capable of supplying energy to the sensor; and
    the sensor mounting head further comprises a first interface, wherein the first interface is electrically coupled to the power source and is capable of supplying energy to the sensor when the sensor is affixed to the sensor mounting head.

11. The apparatus of claim 10, wherein
    the one or more first retaining elements are magnets and the one or more second retaining elements are ferromagnetic elements, or the one or more first retaining elements are magnets and the one or more second retaining elements are magnets, or the one or more first retaining elements are ferromagnetic elements and the one or more second retaining elements are magnets.

12. The apparatus of claim 11 further comprising a radiation shield mechanically coupled to the handle.

13. The apparatus of claim 12, wherein the radiation shield comprises substantially lead.

14. The apparatus of claim 10, wherein the sensor mounting head further comprises one or more retaining straps capable of affixing the sensor to the sensor mounting head.

15. The apparatus of claim 10, wherein the handle comprises a radiation shield capable of reducing electromagnetic radiation to the handle.

16. The apparatus of claim 15, wherein the radiation shield comprises substantially lead.

17. The apparatus of claim 10, wherein the apparatus further comprises a removable biological barrier substantially surrounding the handle, such that the biological barrier reduces the probability of biological material present on the handle from coming into contact with a hand of a user grasping the handle through the biological barrier.

18. The apparatus of claim 10, wherein the first interface comprises a first connector, and the sensor further comprises a second connector such that, when the sensor is affixed to the sensor mounting head, the first connector and the second connector are electrically coupled such that the power source supplies energy to the sensor.

19. The apparatus of claim 18, wherein the handle further comprises a wireless data transmitter wherein: the wireless data transmitter is capable of transmitting data wirelessly to a receiving device; and the wireless data transmitter is electrically coupled to the first connector such that, when the sensor is affixed to the sensor mounting head, the sensor is capable of transmitting data through the first connector to the wireless data transmitter.

20. The apparatus of claim 10, wherein the first interface comprises a first wireless interface, and the sensor further comprises a second wireless interface such that, when the sensor is affixed to the sensor mounting head, the first wireless interface and the second wireless interface are electrically coupled such that the power source supplies energy to the sensor.

21. The apparatus of claim 20, wherein the handle further comprises a wireless data transmitter wherein: the wireless data transmitter is capable of transmitting data wirelessly to a receiving device; and the wireless data transmitter is electrically coupled to the first wireless interface such that, when the sensor is affixed to the sensor mounting head, the sensor is capable of transmitting data through the first wireless interface to the wireless data transmitter.

* * * * *